United States Patent [19]
Brotz

[11] Patent Number: 5,425,747
[45] Date of Patent: Jun. 20, 1995

[54] SUTURE

[76] Inventor: Gregory R. Brotz, P.O. Box 1322, Sheboygan, Wis. 53081

[21] Appl. No.: 134,659

[22] Filed: Oct. 12, 1993

[51] Int. Cl.⁶ ............................................. A61B 17/00
[52] U.S. Cl. .................... 606/228; 606/215; 606/230
[58] Field of Search ............... 606/214, 215, 216, 221, 606/224, 228, 230

[56] References Cited

U.S. PATENT DOCUMENTS

| | | | |
|---|---|---|---|
| 3,123,077 | 3/1964 | Alcamo | 606/228 |
| 4,467,805 | 8/1984 | Fukuda | 606/228 |
| 4,621,639 | 11/1986 | Transue et al. | 606/215 |
| 5,222,976 | 6/1993 | Yoon | 606/223 |

*Primary Examiner*—Gary Jackson
*Attorney, Agent, or Firm*—William Nitkin

[57] ABSTRACT

A suture made of bioabsorbable material is disclosed having a central body member with a plurality of lateral members extending perpendicularly therefrom and in the same general plane with the central body member, each lateral member having a plurality of barb members extending at an acute angle therefrom, allowing the lateral members to be inserted laterally into two sides of a cut in body tissue so that the two sides are joined at an incision junction at the central body member and are retained securely and non-withdrawably in the body tissue by the barb members on such lateral members. Also disclosed is a method for utilizing the suture of this invention.

7 Claims, 2 Drawing Sheets

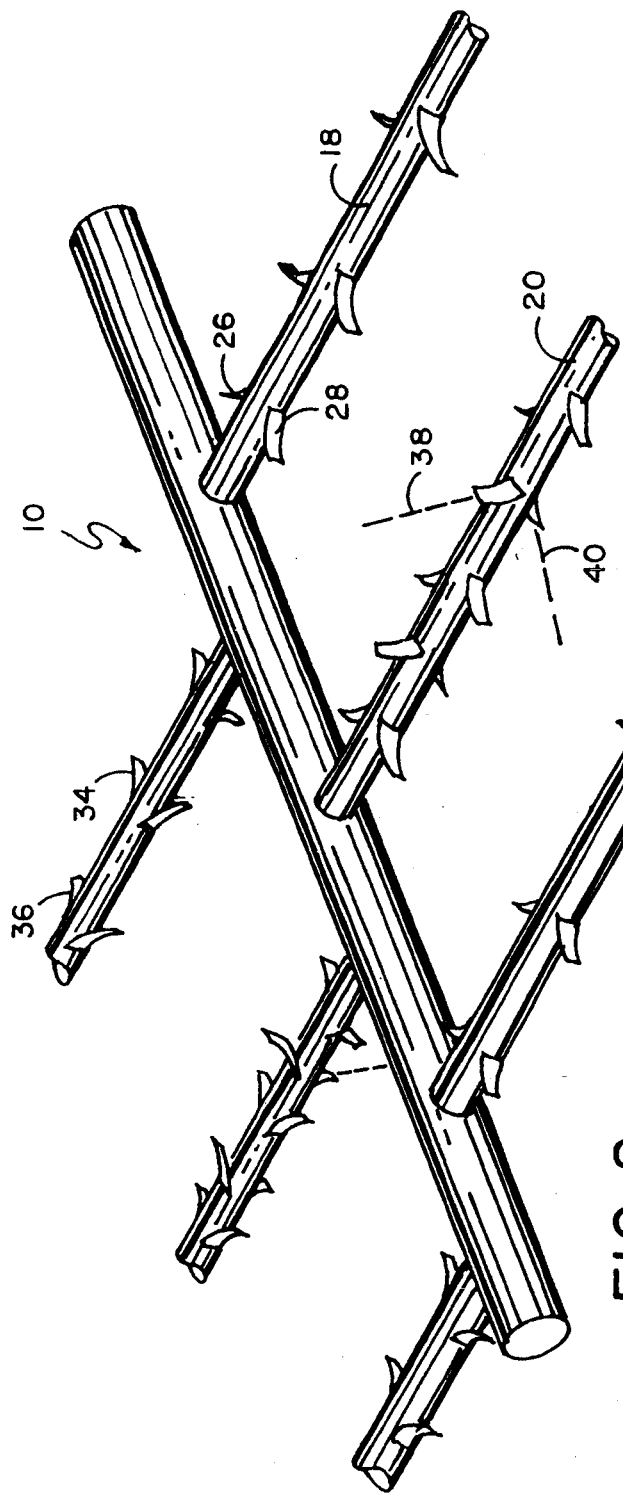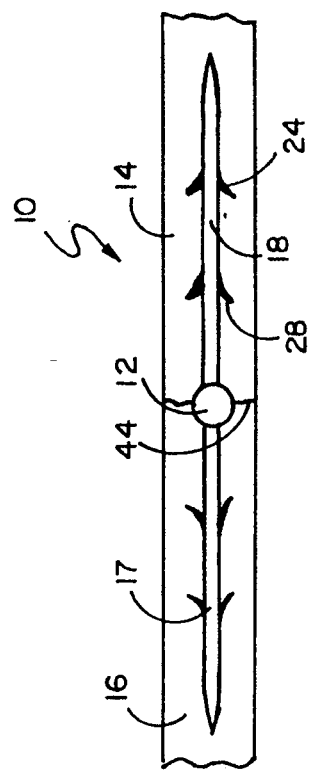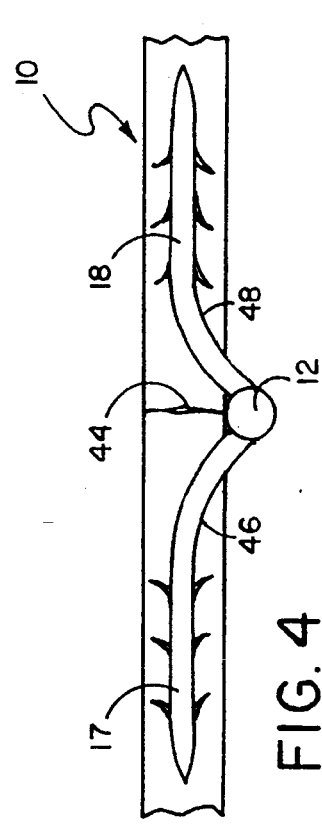

SUTURE

BACKGROUND OF THE INVENTION

1. Field of the Invention

The device of this invention resides in the area of sutures and fasteners for closing the two sides of an incisions or cut in human skin or other body tissue and more particularly relates to a device having a central body member from which extend a plurality of lateral members with multiple barb members formed thereon which lateral members are inserted laterally into the two sides of a cut or incision to join the two sides together at a junction at the central body member.

2. Description of the Prior Art

Sutures for closing incisions or wounds are well known in the prior art. Such sutures or ligatures are often attached to the shank end of a needle and are utilized by physicians to make stitches to close incisions or wounds so that they may heal. Sutures are formed not only of thread-like material, but are also available as a one-piece unit combined with a needle. Sutures are available in a wide variety of monofilament and braided suture material. Sutures can be formed of non-absorbable material such as cat gut, silk nylon, polyester polypropylene, linen, or cotton as well as bioabsorbable synthetic material such as polymers and copolymers of glycolic and lactic acid. Germicides can also be incorporated into the structure of sutures which can be retained by the suture substrate to provide long-lasting germicidal properties.

Also known in the prior art are fasteners which eliminate the need for sutures in many instances. These fasteners are commonly referred to as "staples" and are useful in joining tissue layers laterally, for example, closing wounds in skin or fascia. Such staples are dispensed by implanting devices loaded with such surgical fasteners, the use of which devices can accomplish in very short time what would take many minutes to perform by suturing. Some staples can be made of bioabsorbable materials. The use of such fasteners results in a significantly reduced loss of blood and also lowers the level of trauma to the patient. Such staples can be in the form of metal staples which have arms bent by the fastening device to hook the separated body tissue together. Staples can require the stapling apparatus to have an anvil member which must be positioned under the tissue to be stapled so that the arms of the staple can be bent inwards. Two-part fastening devices also have been used which incorporate a barbed staple, the arms of which are attached to a bottom retaining member. One drawback to employing staples requiring a retainer member be attached to it is that there must be means for positioning such retainer member under the body tissue to be joined, and one must have access to the body tissue both from above and below the body issue. Metal staples applied to the body must also be removed by staple extractors.

Other types of surgical fasteners include skin tacks which are used to join two sides of an incision. Such skin tacks include a barbed tip on each end of the inverted U-shaped tack, the body of which is transversely positioned across an incision or cut, and the tack applied so that the barbed tips engage straight downward into the skin to hold each side of the adjacent layers of body tissue together. In such fastening devices no back retainer is required.

SUMMARY OF THE INVENTION

It is an object of this invention to provide a new type of surgical fastener for joining skin or other body tissue which is separated such as by an incision.

It is a further object that the suture of this invention not require any other instruments for its use.

The structure of this invention consists of a central body member having a plurality of laterally disposed members extending therefrom on opposite sides in a horizontal plane and parallel to one another and perpendicular to the central body member. Disposed on each lateral members is a plurality of barb members which each extend therefrom at a rearwardly disposed acute angle to the direction of insertion. These lateral members, when inserted laterally into the skin or body tissue, remain fixed in position because the barb members, if the skin or body tissue is moved in a direction away from the central body member, will catch the skin or body tissue and prevent such lateral movement. The structure of this invention can be made of bioabsorbable material so that it will dissolve gradually as the cut or incision heals. The suture can have an extremely narrow diameter, yet be stiff enough to be laterally inserted into the skin or other tissue to be joined. The barb members can be disposed either in a plane parallel to the horizontally disposed lateral members on the central body member or, in an alternate embodiment, can be disposed not only parallelly but also perpendicularly to such plane to provide for even greater retention of the suture within the skin or body tissue into which the suture of this invention is inserted.

BRIEF DESCRIPTION OF THE DRAWINGS

FIG. 2 illustrates a perspective view of the suture of this invention having staggered placement of the lateral members.

FIG. 3 illustrates a cross-sectional end view of the suture of FIG. 1.

FIG. 4 illustrates a cross-sectional end view of an alternate embodiment of the suture of this invention having bent lateral members.

DESCRIPTION OF THE PREFERRED EMBODIMENT(S)

Figure 1:
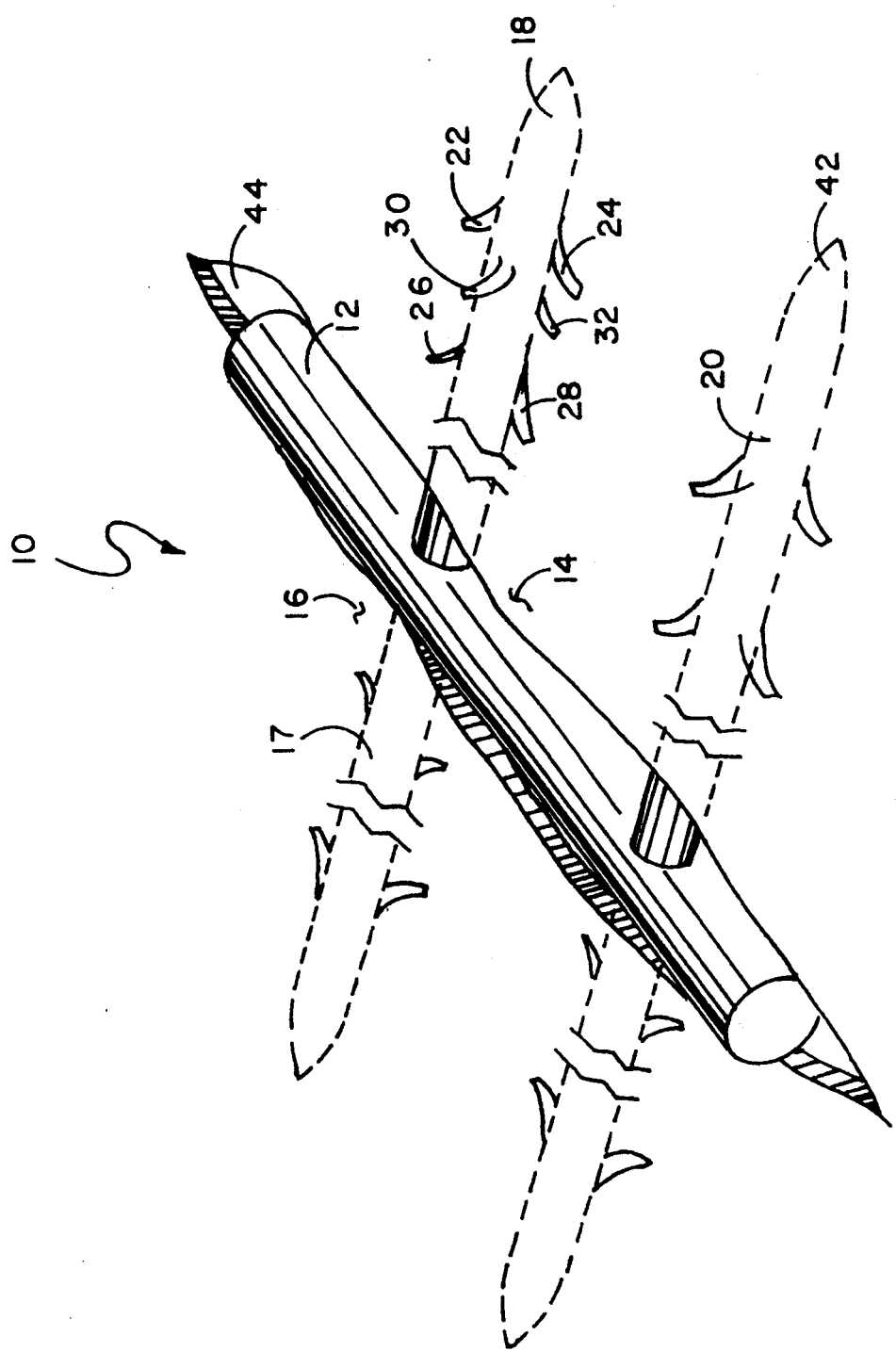
FIG. 1 illustrates a perspective view of the suture of this invention having been inserted laterally into each side of a cut in the skin.

FIG. 1 illustrates a perspective view of suture 10 of this invention within incision 44 having first and second sides 14 and 16 about to be brought together over central body member 12. Although a surgical incision is illustrated, the suture of this invention can also be used to fasten an accidental wound. The device of this invention is shown substantially enlarged in this view, but its size can vary depending on several factors such as the extent of the cut, the type of tissue to be joined, the location of the cut, etc. The suture can be made of bioabsorbable material which is well known in the prior art and should have sufficient stiffness so as to be able to be laterally inserted into the skin or body tissue. In all embodiments of the suture of this invention central member 12 can be of any desired length as can be the lateral members. The central and lateral members can be cut to any length or can be packaged in a variety of pre-cut lengths. Central body member 12 has a plurality of laterally extending lateral members, such as first lateral member 18 which is positioned opposite to second lateral member 17 and parallel to third lateral member 20. Other lateral members can extend from the sides of central body member 12, where the central body member and lateral members, in one embodiment, are all in the same general plane. Formed along each lateral member are a plurality of barb members, such as first and second barb members 22 and 24 and third and fourth barb members 26 and 28. The barb members can be either molded in a barb-like shape or can be formed from acute angular cuts made directly in the bioabsorbable material of the lateral members and with such cut portions pushed outward and separated away from the lateral member. First, second, third and fourth barb members 22, 24, 26 and 28, in one embodiment, are formed parallel to the plane of the lateral members.

In use, first side 14 of the incision is manually held while the lateral members on one side of the central body member are inserted laterally into first side 14. Then the second side 16 is held while the lateral members of the other side of the suture of this invention are inserted laterally into second side 16 with the final step being to urge first and second sides 14 and 16 together to form a junction at central body member 12, which sides are held in place by the plurality of barb members which resist outward movement of the skin or body tissue away from the central body member. Other barb members can also be formed or positioned on the lateral members perpendicular to the plane of the lateral members, such as fifth and sixth barb members 30 and 32 which are seen in FIG. 1. The lateral members can be rounded and have pointed ends 42 to facilitate their lateral insertion into the skin or body tissue.

FIG. 2 illustrates a perspective view of suture 10 of this invention in which the lateral members protrude off central body member 12 in one embodiment in a staggered relationship to one another. On third lateral member 20 are seen dotted lines 40 within the plane of the lateral members showing the barbs extending in that plane whereas dotted lines 38 indicate the plane perpendicular to the plane of the lateral members in which, for example, fifth and sixth barb members 30 and 32 are positioned. The barb members can be formed on any plane around the lateral members as long as, once inserted laterally in the skin/body tissue, they securely retain the suture in place.

FIG. 3 illustrates a cross-sectional end view showing the suture 10 of FIG. 1 inserted into first side 14 and pushed up against second side 16 of incision junction 44. Suture 10 is held in place by the plurality of barb members on the plurality of lateral members such as, for example, barb members 24 and 28 on lateral member 18. In some cases where it is not desirable for central body member 12 to be positioned in the same plane as its lateral members, the central body member can be positioned below such plane, as illustrated in FIG. 4, where the lateral members each are composed of first and second parts, the second part at the junctions with the central body member being angularly bent, such as second parts 46 and 48, thereby positioning the central body member below the plane of the plurality of first parts and incision junction 44.

Although the present invention has been described with reference to particular embodiments, it will be apparent to those skilled in the art that variations and modifications can be substituted therefor without departing from the principles and spirit of the invention.

I claim:

1. A suture assembly for lateral insertion in body tissue having a cut defined therein forming first and second sides of said cut, said suture for joining said first and second sides of said cut at a junction, comprising:
    a central body member having first and second sides and first and second ends;
    a plurality of lateral members each having an outer end disposed perpendicularly to said central body member on said first and second sides of said central body member, said lateral members are in parallel and planar relationship to one another and in planar relationship to said central body member, each lateral member for direct insertion within said cut into the side of said cut adjacent thereto; and
    a plurality of barb members positioned on said lateral members, each extending at an acute angle to said central body member, said barb members preventing outward movement of said body tissue surrounding said lateral members away from said central body member after said lateral insertion of said lateral members into said first and second sides of said cut and positioning of said central body member at said junction of said first and second sides of said cut.

2. The suture of claim 1 wherein said suture is made of bioabsorbable material.

3. The suture of claim 1 wherein said plurality of barb members are formed from acute angular cuts defined in said plurality of lateral members directed away from said central body member.

4. The suture of claim 1 wherein each of said lateral members is comprised of a first part having first and second ends and a second part having first and second ends, said first parts being parallel to one another and forming a perpendicular to said sides of said central body member, each of said second ends of said first parts joined respectively to the first ends of said second parts, each of said second parts having a downward angular bend and each of said second ends of said second parts joined respectively to the sides of said central body member to dispose said central body member in a plane lower than the plane of said first parts of said plurality of lateral members.

5. The suture of claim 1 wherein said lateral members are rounded.

6. The suture of claim 1 wherein said ends of said lateral members are pointed.

7. The method of joining at a junction first and second sides of a cut defined in body tissue, comprising the steps of:
    providing a suture made of bioabsorbable material having a central body member having first and second sides, a plurality of lateral members disposed perpendicularly to said central body member on each side of said central body member, said lateral members in parallel and planar relationship to one another and in planar relationship to said central body member, and a plurality of barb members positioned on said lateral members, each extending at an acute angle to said central body member;
    laterally inserting said lateral members positioned along said first side of said central body member into said first side of said cut;
    laterally inserting said lateral members positioned along said second side of said central body member into said second side of said cut; and positioning said first and second sides of said cut at said junction at said central body member;

engaging the body tissue of said first and second sides of said cut by said positioning of said barb members thereagainst; and preventing outward movement of said first and second sides of said cut away from said central body member by said engagement of said barb members against the body tissue of said first and second sides of said cut.

* * * * *